United States Patent
Capet et al.

(10) Patent No.: US 12,178,671 B2
(45) Date of Patent: Dec. 31, 2024

(54) ULTRASOUND TREATMENT APPLIANCE WITH AUTOMATIC SETPOINT CONTROL

(71) Applicant: SOCIETE POUR LA CONCEPTION DES APPLICATIONS DES TECHNIQUES ELECTRONIQUES, Merignac (FR)

(72) Inventors: Xavier Capet, Cestas (FR); Charles Reche, Bordeaux (FR)

(73) Assignee: SOCIETE POUR LA CONCEPTION DES APPLICATIONS DES TECHNIQUES ELECTRONIQUES, Merignac (FR)

( * ) Notice: Subject to any disclaimer, the term of this patent is extended or adjusted under 35 U.S.C. 154(b) by 1530 days.

(21) Appl. No.: 16/481,716

(22) PCT Filed: Jan. 29, 2018

(86) PCT No.: PCT/FR2018/050198
§ 371 (c)(1),
(2) Date: Jul. 29, 2019

(87) PCT Pub. No.: WO2018/138453
PCT Pub. Date: Aug. 2, 2018

(65) Prior Publication Data
US 2020/0022723 A1    Jan. 23, 2020

(30) Foreign Application Priority Data

Jan. 30, 2017  (FR) .......................................... 1750730

(51) Int. Cl.
*A61C 1/07* (2006.01)
*A61B 17/32* (2006.01)
(Continued)

(52) U.S. Cl.
CPC ........ *A61C 1/07* (2013.01); *A61B 17/320068* (2013.01); *A61C 1/0015* (2013.01);
(Continued)

(58) Field of Classification Search
CPC . A61C 1/07; A61C 1/0015; A61B 17/320068; A61B 2017/0003;
(Continued)

(56) References Cited

U.S. PATENT DOCUMENTS

| | | | |
|---|---|---|---|
| 2009/0047624 A1* | 2/2009 | Tsai ..................... | A61C 1/0007 433/119 |
| 2010/0231090 A1 | 9/2010 | Klopfenstein et al. | |

(Continued)

FOREIGN PATENT DOCUMENTS

EP    2138123 A1    12/2009

OTHER PUBLICATIONS

Brochure: "Piezotome Solo," Satelec Acteon, Dec. 31, 2011, 6 Pages.
(Continued)

*Primary Examiner* — Nicholas D Lucchesi
(74) *Attorney, Agent, or Firm* — Workman Nydegger

(57) ABSTRACT

An ultrasound treatment appliance comprising a surgical handpiece, an ultrasound insert, and an ultrasound generator, the handpiece including a piezoelectric transducer connected to the ultrasound insert and a piezoelectric motor connected to the ultrasound generator. The piezoelectric motor transmits ultrasound waves to the insert, which waves are defined as a function of current and voltage setpoint signals delivered by the ultrasound generator to the piezoelectric motor. The appliance also includes a module for controlling the amplitudes of the setpoint signals and configured to increase or decrease the amplitudes of the current and voltage setpoint signals when the variation in the (Continued)

impedance of the ultrasound signal is greater than a predetermined impedance variation value and when the variation in the frequency of the ultrasound signal is greater than or less than the predetermined frequency variation value.

10 Claims, 5 Drawing Sheets

(51) Int. Cl.
    *A61C 1/00*     (2006.01)
    *A61B 17/00*     (2006.01)
(52) U.S. Cl.
    CPC ............. *A61B 2017/0003* (2013.01); *A61B 2017/0011* (2013.01); *A61B 2017/00185* (2013.01)
(58) Field of Classification Search
    CPC .. A61B 2017/0011; A61B 2017/00185; H10N 30/802
    See application file for complete search history.

(56) References Cited

U.S. PATENT DOCUMENTS

| | | |
|---|---|---|
| 2013/0282038 A1 | 10/2013 | Pannaher et al. |
| 2015/0150647 A1* | 6/2015 | Chevalier ............... A61C 3/02 433/27 |
| 2015/0188023 A1* | 7/2015 | Pond .................... A61C 1/0015 310/317 |
| 2016/0120563 A1 | 5/2016 | Messerly et al. |
| 2016/0325121 A1 | 11/2016 | Kawashima et al. |

OTHER PUBLICATIONS

Brochure: "Livret Clinique Chirurgie," Satelec Acteon, Dec. 31, 2012, 99 Pages.

International Search Report and Written Opinion from PCT Application No. PCT/FR2018/050198, Apr. 6, 2018.

* cited by examiner

ULTRASOUND TREATMENT APPLIANCE WITH AUTOMATIC SETPOINT CONTROL

BACKGROUND OF THE INVENTION

The present invention relates to ultrasound treatment appliances used in particular in the field of dentistry, such as appliances for scaling, biofilm removal, or drilling (cavities or preparing prostheses), or in the field of surgery (e.g.: maxillofacial surgery and stomatology, or orthopedic surgery). Such appliances comprise instruments that vibrate at ultrasound frequencies.

Ultrasound treatment appliances generally comprise a surgical handpiece, an insert or ultrasonic tool, and an ultrasound generator. The handpiece has a piezoelectric transducer constituted by a distal portion on which the ultrasound insert is fastened and a piezoelectric motor connected to the ultrasound generator and mechanically coupled to the distal portion. The piezoelectric motor transmits ultrasound waves to the insert, which waves are defined as a function of setpoint current and voltage signals delivered by the ultrasound generator to the piezoelectric motor. The setpoint signals are set at the beginning of treatment, with their values being determined as a function of the type of treatment that is to be undertaken. For example, in the field of dentistry, for periodontal debridement, the current and voltage setpoints are much lower than those needed for scaling. Consequently, for each type of dental treatment, there exists an appropriate setpoint for controlling the ultrasound waves.

Nevertheless, during treatment, the ultrasound insert may encounter media or materials that have different hardnesses. For example, the insert may encounter both soft tissue such as a gum, a muscle, etc., and harder tissue such as a bone. The setpoint value is the same for any one type of treatment, and this applies regardless of the media or materials that are encountered by the insert during the treatment.

Consequently, during any given treatment, it can happen that the setpoints determining the amplitude of the current and voltage setpoint signals delivered by the ultrasound generator are not appropriate or optimum for the medium or material encountered by the insert, which may lead, by way of example, to risks of damaging fragile portions that come into contact with the insert or to a lack of effective treatment when the insert is in contact with materials that are very resistant.

OBJECT AND SUMMARY OF THE INVENTION

An object of the present invention is to remedy the above-mentioned drawbacks and to propose a solution that makes it possible to adapt the setpoint signals delivered to the transducer to match the hardness of the material in contact with the ultrasound insert.

This object is achieved by an ultrasound treatment appliance comprising at least a surgical handpiece, an ultrasound insert, and an ultrasound generator, the handpiece including a piezoelectric transducer constituted by a distal portion having the ultrasound insert fastened thereto and a piezoelectric motor connected to the ultrasound generator and mechanically coupled to the distal portion, said piezoelectric motor transmitting ultrasound waves to the insert, which waves are defined as a function of current and voltage setpoint signals delivered by the ultrasound generator to the piezoelectric motor, the appliance being characterized in that it further comprises a module for controlling the amplitudes of the setpoint signals and configured to:

calculate a variation in the frequency and the impedance of the control signal in the piezoelectric transducer;

compare the impedance variation of the ultrasound signal with a predetermined impedance variation value;

compare the variation in the frequency of the ultrasound signal with a predetermined frequency variation value;

increase the amplitudes of the current and voltage setpoint signals delivered by the ultrasound generator when the calculated variation in the impedance of the ultrasound signal is greater than the predetermined impedance variation value and when the calculated variation in the frequency of the ultrasound signal is greater than the predetermined frequency variation value; and decrease the amplitudes of the current and voltage setpoint signals delivered by the ultrasound generator when the calculated variation in the impedance of the ultrasound signal is greater than the predetermined impedance variation value and when the calculated variation in the frequency of the ultrasound signal is less than the predetermined frequency variation value.

Thus, the dental treatment appliance of the invention is capable of detecting a change in the hardness of the material in contact with the ultrasound insert and of automatically modifying the amplitudes of the setpoint signals delivered to the transducer as a function of the hardness of the material. The appliance of the invention thus provides automatic assistance to the practitioner's action so the practitioner thus benefits from improved safety and greater effectiveness in using the appliance.

The present invention is also remarkable in that the change in hardness is detected without any need to provide the handpiece with additional sensors. Specifically, the change in hardness is detected as a function of variations of impedance and frequency in the transducer, which variations are dependent on the material in contact with the ultrasound insert. The insert thus acts as a sensor, thereby optimizing measurement accuracy.

The variation in the frequency and the impedance of the ultrasound signal in the piezoelectric transducer comprises measuring at least two mean values of the frequency and of the impedance of the ultrasound signal in the piezoelectric transducer over a determined period, the variation in the frequency of the ultrasound signal being calculated between two measured mean values of the frequency of the ultrasound signal, the variation in the impedance of the ultrasound signal being calculated between two measured values of the impedance of the ultrasound signal. The mean values of the frequency and the impedance of the ultrasound signal in the piezoelectric transducer may be measured once every 100 milliseconds (ms). Under such circumstances, in an aspect of the method of the invention, the predetermined frequency variation value may be equal to 12 hertz (Hz), and the predetermined impedance variation value may be equal to 26 ohms (a).

According to yet another aspect of the appliance of the invention, the amplitudes of the current and voltage setpoint signals delivered by the ultrasound generator are increased by 20% when the calculated variation in the frequency of the ultrasound signal is greater than the predetermined frequency variation value and when the calculated variation in the impedance of the ultrasound signal is greater than the predetermined impedance variation value. Likewise, the amplitudes of the current and voltage setpoint signals delivered by the ultrasound generator are decreased by 20% when the calculated variation in the frequency of the ultrasound signal is less than the predetermined frequency variation value and when the calculated variation in the impedance of the ultrasound signal is greater than the predetermined impedance variation value.

The present invention also provides a method of controlling setpoint signals in an ultrasound treatment appliance comprising at least a surgical handpiece, an ultrasound insert, and an ultrasound generator, the handpiece including a piezoelectric transducer constituted by a distal portion having the ultrasound insert fastened thereto and a piezoelectric motor connected to the ultrasound generator and mechanically coupled to the distal portion, said piezoelectric motor transmitting ultrasound waves to the insert, which waves are defined as a function of current and voltage setpoint signals delivered by the ultrasound generator to the piezoelectric motor, the method being characterized in that it comprises the following steps:
calculating the variation in the frequency and the impedance of the control signal in the piezoelectric transducer;
comparing the impedance variation of the ultrasound signal with a predetermined impedance variation value;
comparing the variation in the frequency of the ultrasound signal with a predetermined frequency variation value;
increasing the amplitudes of the current and voltage setpoint signals delivered by the ultrasound generator when the calculated variation in the impedance of the ultrasound signal is greater than the predetermined impedance variation value and when the calculated variation in the frequency of the ultrasound signal is greater than the predetermined frequency variation value; and
decreasing the amplitudes of the current and voltage setpoint signals delivered by the ultrasound generator when the calculated variation in the impedance of the ultrasound signal is greater than the predetermined impedance variation value and when the calculated variation in the frequency of the ultrasound signal is less than the predetermined frequency variation value.

In another aspect of the method of the invention, the amplitudes of the current and voltage setpoint signals delivered by the ultrasound generator are increased by 20% when the calculated variation in the frequency of the ultrasound signal is greater than the predetermined frequency variation value and when the calculated variation in the impedance of the ultrasound signal is greater than the predetermined impedance variation value. Likewise, the amplitudes of the current and voltage setpoint signals delivered by the ultrasound generator are decreased by 20% when the calculated variation in the frequency of the ultrasound signal is less than the predetermined frequency variation value and when the calculated variation in the impedance of the ultrasound signal is greater than the predetermined impedance variation value.

In yet another aspect of the method of the invention, the step of calculating variation in the frequency and the impedance of the ultrasound signal in the piezoelectric transducer comprises measuring at least two mean values of the frequency and of the impedance of the ultrasound signal in the piezoelectric transducer over a determined period, the variation in the frequency of the ultrasound signal being calculated between two measured mean values of the frequency of the ultrasound signal, the variation in the impedance of the ultrasound signal being calculated between two measured mean values of the impedance of the ultrasound signal.

The mean values of the frequency and the impedance of the ultrasound signal in the piezoelectric transducer may be measured once every 100 ms. Under such circumstances, in an aspect of the method of the invention, the predetermined frequency variation value may be equal to 12 Hz, and the predetermined impedance variation value may be equal to 26Ω).

BRIEF DESCRIPTION OF THE DRAWINGS

Other characteristics and advantages of the invention appear from the following description of particular embodiments of the invention given as non-limiting examples and with reference to the accompanying drawings, in which.

DETAILED DESCRIPTION OF EMBODIMENTS OF THE INVENTION

Figure 1:
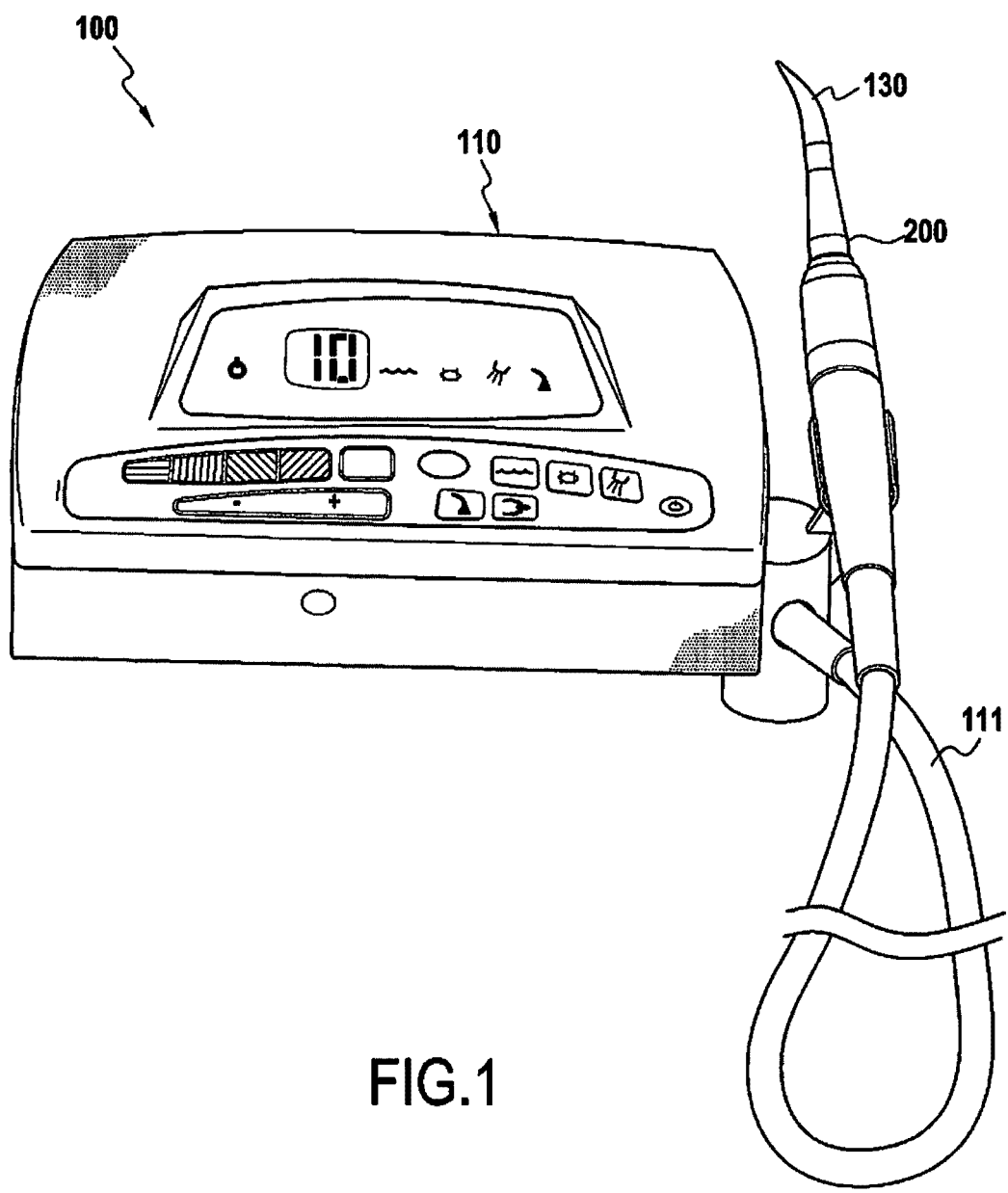
FIG. 1 is a diagrammatic view of an ultrasound dental treatment appliance.

The ultrasound treatment appliance of the invention has applications in the general field of surgery and more particularly in the field of dental surgery or treatment and also in the field of bone surgery (e.g. maxillofacial or orthopedic surgery). FIG. 1 shows an ultrasound treatment appliance 100 comprising an ultrasound generator 110 connected to a handpiece 200 by a cord 111. A sonotrode or ultrasound insert 130 is mounted on the top or distal portion of the handpiece 200. In well-known manner, the handpiece 200 has a transducer (not shown in FIG. 1) made of a piezoelectric material and mechanically coupled to the insert 130 so as to transmit thereto ultrasound waves that are defined as a function of current and voltage setpoint signals delivered by the ultrasound generator.

Figure 2:
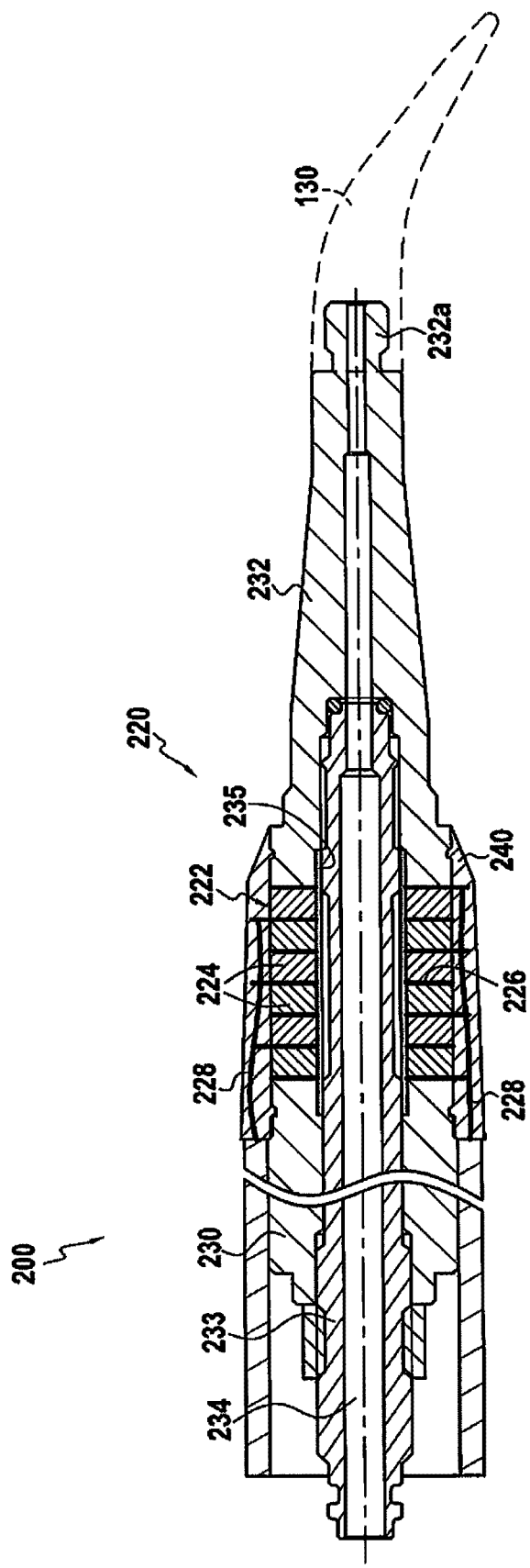
FIG. 2 is a diagrammatic section view of the handpiece of the FIG. 1 appliance.

FIG. 2 is a longitudinal section view showing the internal structure of the piezoelectric transducer 220 arranged in the handpiece 200. The piezoelectric transducer comprises in particular a proximal portion 230, a distal portion 232, and a piezoelectric motor 222 interposed between the distal and proximal portions. In the presently-considered example, the proximal and distal portions 230 and 232 correspond respectively to a reaction mass and to an amplifier. The reaction mass 230 and the amplifier 232 bear mechanically against the piezoelectric motor 222 so that it is stressed mechanically.

In this example, the piezoelectric motor 222 is constituted by six piezoelectric ceramics 224 of annular shape arranged against one another under stress between the reaction mass 230 and the amplifier 232. Each of the ceramics 224 is covered in an electrically conductive coating (e.g. silvering) and seven conductive annular plates 226 are interposed between the ceramics 224 so as to connect the power supply cables 228 electrically with the piezoelectric ceramics 224. When the ceramics 224 of the piezoelectric motor 222 are subjected to an electric signal transmitted by the cables 228 connected to the ultrasound generator, they generate mechanical vibration in the form of ultrasound waves. These ultrasound waves are then transmitted via the distal portion 232 of the piezoelectric transducer 220 to the ultrasound insert 130 (not shown in FIG. 2) mounted at the free end 232*a* of the distal portion 232.

In this example, an electrically insulating covering 240 is also arranged around the piezoelectric motor 222 specifically to protect and insulate the cables 228. Furthermore, a rigid prestress rod 233 is arranged in the center of the piezoelectric transducer 220. An electrically insulating element 235 is also arranged between the prestress rod 233 and the piezoelectric motor 222. An irrigation duct 234 is also formed at the center of the prestress rod 233 so as to be able to cause a liquid to flow through the handpiece and be discharged from the insert 130.

Figure 3:
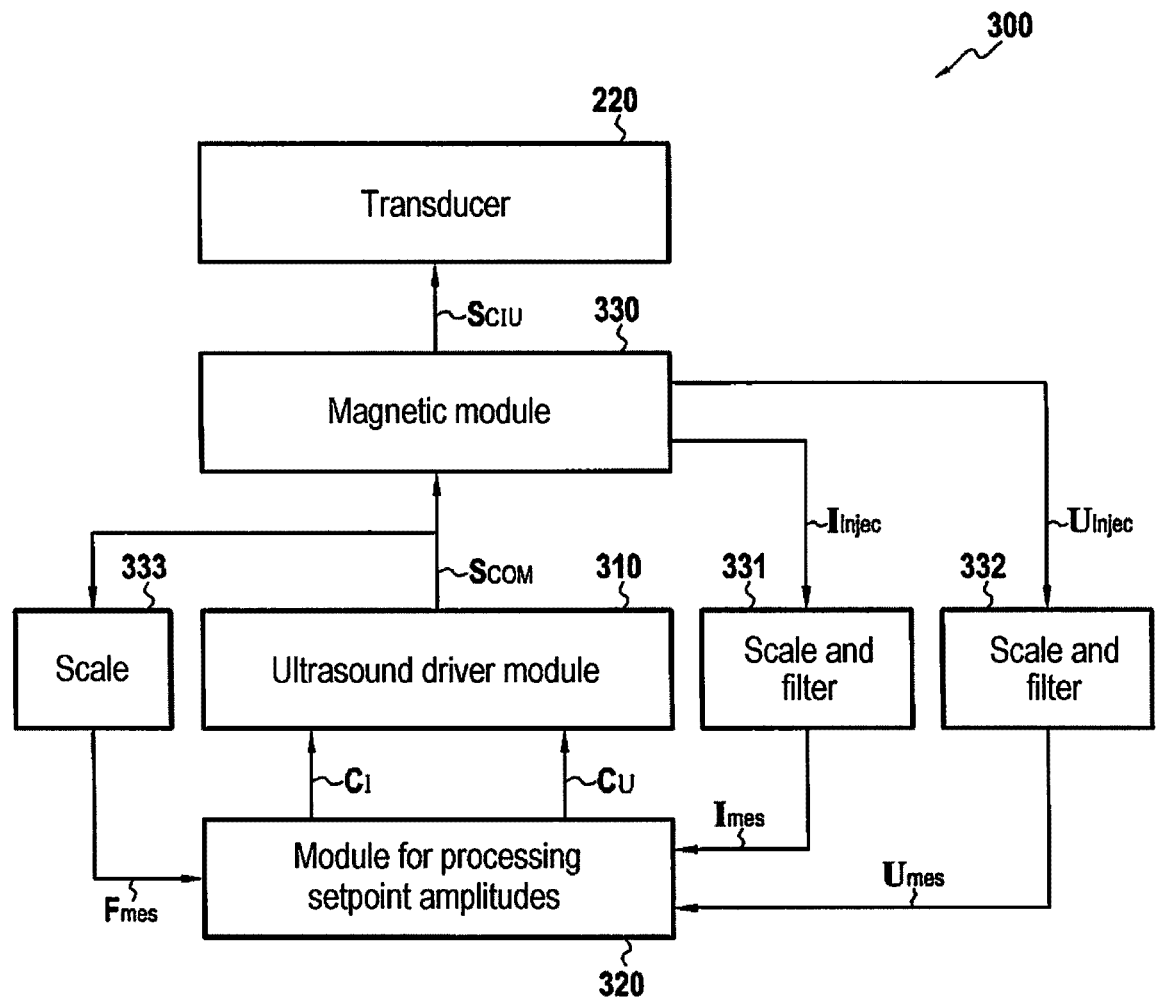
FIG. 3 is a block diagram of an electronic circuit for controlling the ultrasound generator of the FIG. 1 appliance in accordance with an implementation of the invention.

In accordance with the invention, the ultrasound treatment appliance is also suitable for measuring variation in the impedance and the amplitude of the ultrasound signal in the piezoelectric transducer and for modifying the setpoint signals delivered by the ultrasound generator when any variation in the impedance of the ultrasound signal exceeds a predetermined value for impedance variation and when any variation in the frequency of the ultrasound signal goes below or above a predetermined value for impedance variation. To this end, the treatment appliance includes a module for processing the amplitude of the setpoint signals that is configured to perform the operations mentioned above. FIG. 3 is a block diagram of an electronic control circuit 300 for controlling the ultrasound generator fitted with a module for processing the amplitude of the setpoint signals in accordance with an implementation of the invention. The control circuit 300 comprises an ultrasound driver module 310, which is configured to send current and voltage setpoint signals $S_{CIU}$ to the transducer 220 in the handpiece via the cables 228, which signals define the frequency and the amplitude of the ultrasound waves produced by the piezoelectric motor of the transducer, the speed of vibration of the piezoelectric motor being a direct function of the electric current flowing therethrough, while the force needed for the vibration is a direct function of the power supply voltage. The setpoint signals $S_{CIU}$ are initially defined as a function of the type of treatment that is to be performed. The current and voltage setpoint signals $S_{CIU}$ are transmitted to the transducer via a magnetic module 330 that comprises a transformer (not shown in FIG. 3). The setpoint signals $S_{COM}$ delivered by the ultrasound driver module 310 are transformed by the magnetic module into current and voltage setpoint signals $S_{CIU}$. In accordance with the invention, the electronic control circuit 300 also includes a module for controlling the amplitude of the setpoint signals 320, which module measures variation in the frequency and in the impedance of the ultrasound signal in the piezoelectric transducer. For this purpose, the module 320 receives signals Imes and Umes corresponding respectively to the current and to the voltage in the transducer. The image of the current and of the voltage in the transducer 220 is obtained by measuring the mean value of the current Iinjec and the mean value of the voltage Uinjec as injected into the transducer. The injected signals Iinjec and Uinjec are taken from the primary of the magnetic module 330. After these signals have been scaled and filtered by respective modules 331 and 332, measurement signals are obtained for the current and the voltage Imes and Umes in the transducer. The measurement of the current and of the voltage in the transducer can thus be performed without any need to connect to a terminal of the transducer, i.e. without any additional cabling in the ultrasound appliance. The frequency and the impedance of the ultrasound signal in the transducer vary as a function of the hardness of the material in contact with the ultrasound insert. The image of the frequency in the transducer 220 is obtained form the setpoint signals $S_{COM}$ delivered by the ultrasound driver module 310. After scaling by the module 333, a signal Fmes is obtained that is a measurement of the frequency in the transducer.

The module 320 calculates the impedance in the transducer from the signals Imes and Umes. The module 320 also receives the signal Fmes corresponding to the frequency in the transducer. The module 320 can thus continuously measure the impedance and the frequency of the signal in the transducer and can deduce therefrom a mean value over a determined period, e.g. once every 100 ms. The module 320 calculates variation in the impedance and in the frequency on the basis of two consecutive measurements.

Figure 4:
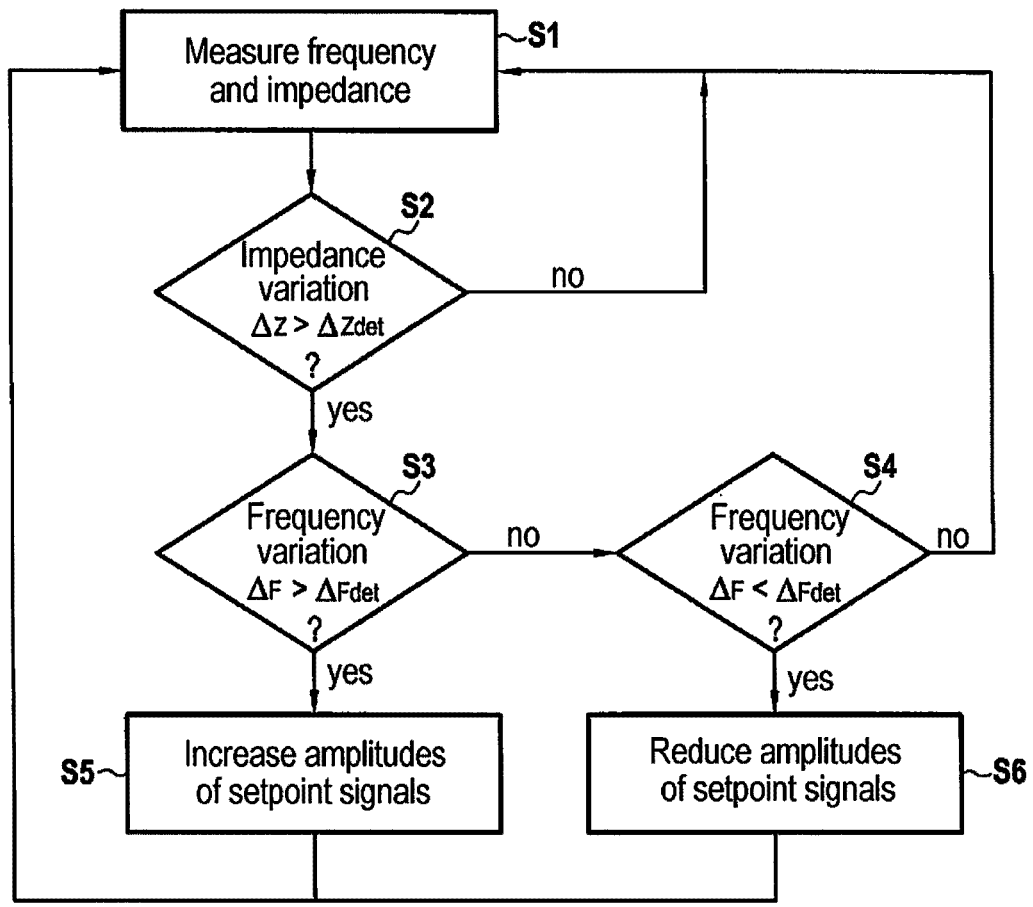
FIG. 4 is a flow chart showing steps of a method of controlling setpoint signals in an ultrasound treatment appliance in accordance with an implementation of the invention.

With reference to FIG. 4, there follows a description of the steps of controlling the setpoints as performed by the module 320 for controlling the amplitudes of the setpoint signals. As mentioned above, the module 320 determines a mean measurement value for the impedance and for the frequency of the signal in the transducer over a determined period and calculates variation therein between two consecutive mean measurement values (step S1). The module 320 compares the impedance variation $\Delta Z$ that is calculated with a predetermined impedance variation value $\Delta Z$det (step S2). If the calculated impedance variation $\Delta Z$ is less than the predetermined impedance variation value $\Delta Z$det, the module 320 leaves the setpoint signals unchanged. If the calculated impedance variation $\Delta Z$ is greater than the predetermined impedance variation value $\Delta Z$det, the module 320 compares the calculated frequency variation $\Delta F$ with a predetermined frequency variation value $\Delta F$det (steps S3 and S4). More precisely, the module 320 determines whether the calculated frequency variation $\Delta F$ is greater than the predetermined frequency variation value $\Delta F$det (step S3). If so, the module 320 sends control signals CI and CU to the setpoint signal driver module 310 so that it increases the amplitude of the current and voltage setpoint signal $S_{CIU}$ delivered to the transducer 220 (step S5). Otherwise, the module 320 determines whether the calculated frequency variation $\Delta F$ is less than the predetermined frequency variation value $\Delta F$det (step S4). If so, the module 320 then controls signals CI and CU to the setpoint signal driver module 310 so that it reduces the amplitudes of the current and voltage setpoint signals $S_{CIU}$ delivered to the transducer 220 (step S6). Otherwise, the module 320 leaves the setpoint signals unchanged. The steps S3 and S4 may be performed in any order.

Any increase or decrease in the amplitudes of the setpoint signals is applied for a determined control period, e.g. 415 ms. Once the control period has elapsed, the method returns to step S1.

Figure 5:
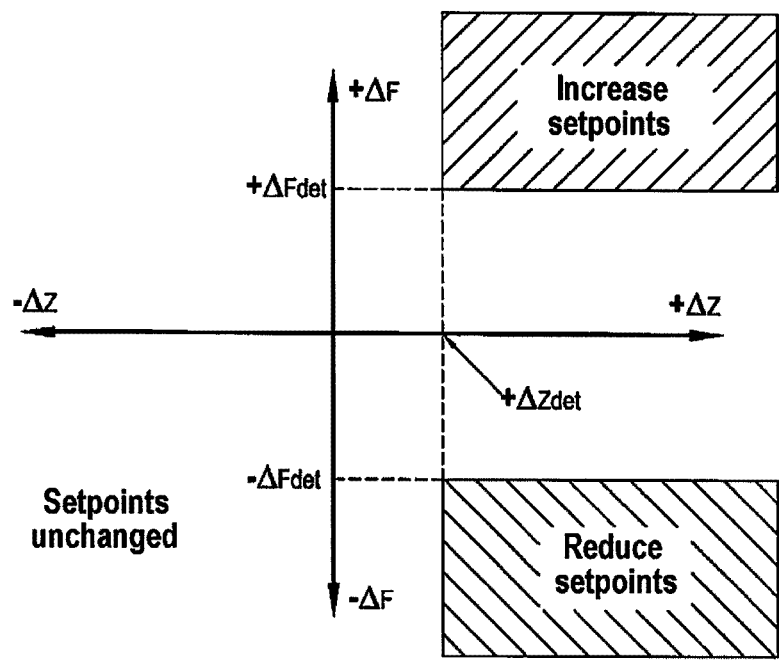
FIG. 5 is a graph showing the conditions for controlling the amplitude of setpoint signals in accordance with the invention.

FIG. 5 is a graph showing the conditions for controlling the amplitudes of the current and voltage setpoint signals as a function of variation in the impedance $\Delta Z$ and in the frequency $\Delta F$ of the ultrasound signal in the transducer, as described above.

The amplitude control of the setpoint signals is applicable to ultrasound signals of constant amplitude and to ultrasound signals that are modulated. If they are modulated, the modulation frequency is preferably greater than or equal to a determined value so as to enable a mean impedance measurement value and the frequency of the signal in the transducer to be determined. For example, when the module 320 determines a mean measurement value over a period of 100 ms, the modulation frequency of the ultrasound signal should be greater than or equal to 25 Hz.

By way of non-limiting example, after experimentation, the predetermined value for impedance variation $\Delta Zdet$ may be set at $26\Omega$ while the predetermined value for frequency variation $\Delta Fdet$ may be set at 12 Hz, so as to be able to determine a mean measurement value for the impedance and the frequency of the signal in the transducer once every 100 ms. Still by way of non-limiting example, any increase or decrease in the amplitudes of the setpoint signals may be set at 20% of the initial setpoint value, i.e. the value set in the ultrasound treatment appliance as a function of the selected type of treatment. The above-mentioned values are determined for an ultrasound treatment appliance that is to perform dental treatment. These values may naturally be different with other types of surgical treatment, such as for maxillofacial surgery or for orthopedic surgery.

Figure 6:
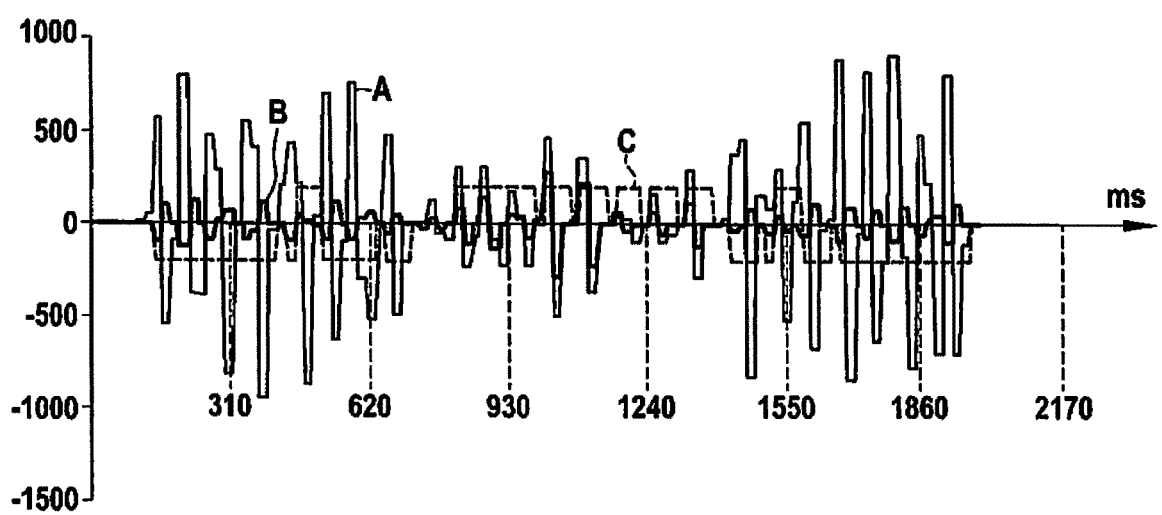
FIG. 6 is an example of performance of the method of the invention for controlling setpoint signal amplitudes.

FIG. 6 shows an example of controlling the amplitudes of setpoint signals in accordance with the invention in an ultrasound dental treatment appliance, specifically the "Piezotome Solo" appliance sold by the supplier Satelec® for pre-implantation surgery. In FIG. 6, curve A shows the impedance variation $\Delta Z$ measured in the transducer, the curve B shows the frequency variation $\Delta F$ measured in the transducer, and the curve C shows the control that is applied to the amplitudes of the current and voltage setpoint signals that are delivered to the transducer. The increases in the amplitudes of the setpoint signals correspond to those portions of the curve C that lie above the abscissa axis. The decreases in the amplitudes of the setpoint signals correspond to those portions of the curve C that are below the abscissa axis. The portions of the curve C that coincide with the abscissa axis correspond to instants at which the amplitudes of the setpoint signals are not modified.

The module for controlling the amplitudes of the setpoint signals 320 may be deactivated while applying the settings for the ultrasound treatment appliance.

The invention claimed is:

1. An ultrasound treatment appliance comprising:
a surgical handpiece,
an ultrasound insert,
an ultrasound generator, and
an electronic control circuit for controlling the ultrasound generator;
wherein the handpiece includes a piezoelectric transducer including a distal portion having the ultrasound insert fastened thereto and a piezoelectric motor connected to the ultrasound generator and mechanically coupled to the distal portion,
wherein the piezoelectric motor is arranged to transmit ultrasound waves to the insert,
wherein said ultrasound waves are transmitted by the piezoelectric motor based on current and voltage setpoint signals delivered by the ultrasound generator to the piezoelectric motor,
wherein the electronic control circuit is configured to:
send the current and voltage setpoint signals to the transducer of the handpiece via cables, the current setpoint signal based on a speed of vibration of the piezoelectric motor and the voltage setpoint signal based on force required for the vibration of the piezoelectric motor;
calculate a variation in frequency and impedance of a control signal in the piezoelectric transducer, the variation in the frequency being calculated between two consecutively measured mean values of the frequency of the control signal and the variation in the impedance being calculated between two consecutively measured mean values of the impedance of the ultrasound signal;
compare the impedance variation of the ultrasound signal with a predetermined impedance variation value;
compare the variation in the frequency of the ultrasound signal with a predetermined frequency variation value;
automatically increase amplitudes of the current and voltage setpoint signals delivered by the ultrasound generator when the calculated variation in the impedance of the ultrasound signal is greater than the predetermined impedance variation value and when the calculated variation in the frequency of the ultrasound signal is greater than the predetermined frequency variation value; and
automatically decrease the amplitudes of the current and voltage setpoint signals delivered by the ultrasound generator when the calculated variation in the impedance of the ultrasound signal is greater than the predetermined impedance variation value and when the calculated variation in the frequency of the ultrasound signal is less than the predetermined frequency variation value.

2. The appliance according to claim 1, wherein the mean values of the frequency and the impedance of the ultrasound signal in the piezoelectric transducer are measured once every 100 ms.

3. The appliance according to claim 2, wherein the predetermined frequency variation value is equal to 12 Hz.

4. The appliance according to claim 2, wherein the predetermined impedance variation value is equal to $26\Omega$.

5. The appliance according to claim 1, wherein the amplitudes of the current and voltage setpoint signals delivered by the ultrasound generator are increased by 20% when the calculated variation in the frequency of the ultrasound signal is greater than the predetermined frequency variation value and when the calculated variation in the impedance of the ultrasound signal is greater than the predetermined impedance variation value, and
wherein the amplitudes of the current and voltage setpoint signals delivered by the ultrasound setpoint generator are decreased by 20% when the measured variation in the frequency of the ultrasound signal is less than the predetermined frequency variation value and when the measured variation in the impedance of the ultrasound signal is greater than the predetermined impedance variation value.

6. The appliance according to claim 1, wherein the piezoelectric motor is interposed between the distal portion and a proximal portion of the piezoelectric transducer, the proximal portion including a reaction mass and the distal portion including an amplifier.

7. The appliance according to claim 6, wherein the reaction mass and the amplifier bear mechanically against the piezoelectric motor.

8. The appliance according to claim 7, wherein the piezoelectric motor includes six piezoelectric ceramics of annular shape arranged against one another under stress between the reaction mass and the amplifier.

9. The appliance according to claim 1, wherein the electronic control circuit further includes:
an ultrasound driver module configured to send the current and voltage setpoint signals to the piezoelectric transducer; and a magnetic module configured to transform the current and voltage setpoint signals obtained from the ultrasound driver module.

10. The appliance according to claim 9, wherein the electronic control circuit further includes a module for controlling the amplitudes of the current and voltage setpoint signals, the module configured to:
- receive a frequency signal from the ultrasound driver module, the frequency signal corresponding to the ultrasound signal in the piezoelectric transducer;
- calculate impedance in the piezoelectric transducer from current and voltage signals obtained from the magnetic module; and
- continuously measure the frequency and the impedance of the control signal in the piezoelectric transducer.

* * * * *